(12) United States Patent
VanCamp et al.

(10) Patent No.: US 7,927,346 B2
(45) Date of Patent: Apr. 19, 2011

(54) DIVERSION DEVICE TO INCREASE CEREBRAL BLOOD FLOW

(75) Inventors: Daniel VanCamp, Covington, WA (US); Eric D. Nielson, Bellevue, WA (US)

(73) Assignees: Stryker Corporation, Kalamazoo, MI (US); Stryker NV Operations Limited, Limerick (IE)

( * ) Notice: Subject to any disclaimer, the term of this patent is extended or adjusted under 35 U.S.C. 154(b) by 213 days.

(21) Appl. No.: 10/937,916

(22) Filed: Sep. 10, 2004

(65) Prior Publication Data

US 2006/0058833 A1 Mar. 16, 2006

(51) Int. Cl.
*A61M 29/00* (2006.01)
(52) U.S. Cl. .................. 606/200; 606/194; 128/887
(58) Field of Classification Search .......... 606/200, 606/191, 194; 604/507, 509; 528/272; 264/328.17; 128/887, 889; 623/2.2, 23.64–23.7
See application file for complete search history.

(56) References Cited

U.S. PATENT DOCUMENTS

| | | | |
|---|---|---|---|
| 4,601,706 A | 7/1986 | Aillon | |
| 4,990,156 A | 2/1991 | Lefebvre | |
| 5,108,418 A | 4/1992 | Lefebvre | |
| 5,375,612 A * | 12/1994 | Cottenceau et al. | 128/899 |
| 5,437,633 A | 8/1995 | Manning | |
| 5,458,574 A | 10/1995 | Machold et al. | |
| 5,599,329 A | 2/1997 | Gabbay | |
| 5,649,953 A | 7/1997 | Lefebvre | |
| 5,683,411 A | 11/1997 | Kavteladze et al. | |
| 5,702,368 A | 12/1997 | Stevens et al. | |
| 5,800,375 A | 9/1998 | Sweezer et al. | |
| 5,820,593 A | 10/1998 | Safar et al. | |
| 5,938,683 A | 8/1999 | Lefebvre | |
| 5,997,557 A | 12/1999 | Barbut et al. | |
| 6,106,548 A * | 8/2000 | Roubin et al. | 623/1.15 |
| 6,160,084 A * | 12/2000 | Langer et al. | 528/272 |
| 6,231,544 B1 | 5/2001 | Tsugita et al. | |
| 6,231,551 B1 | 5/2001 | Barbut | |
| 6,352,667 B1 * | 3/2002 | English | 264/328.17 |
| 6,361,545 B1 * | 3/2002 | Macoviak et al. | 606/200 |

(Continued)

FOREIGN PATENT DOCUMENTS

| | | |
|---|---|---|
| FR | 2 567 405 A1 | 1/1986 |
| WO | WO0027292 A1 | 5/2000 |
| WO | WO2005/102221 | * 11/2005 |

OTHER PUBLICATIONS

Walters, "Intracranial Pressure and Cerebral Blood Flow", 1998, Physiology, Issue 8, Article 4, pp. 1,8.*

(Continued)

*Primary Examiner* — Todd E Manahan
*Assistant Examiner* — Katherine M Dowe
(74) *Attorney, Agent, or Firm* — Vista IP Law Group LLP

(57) ABSTRACT

Methods and devices provide for temporary partial aortic occlusion to achieve diversion of blood flow to the brain in patients suffering from cerebral ischemia. The device can include an expandable frame with a membrane mounted on a first portion of the frame. The membrane can have at least one opening. In some embodiments, the membrane has an outer region and an inner region, and an opening in the inner region. In use, the frame can expand to conform to the inner walls of the aorta and the membrane can at least partially occlude the aorta thereby increasing cerebral perfusion. The frame can include one or more anchors to aid in maintaining the device in position against the arterial blood flow pressure.

23 Claims, 5 Drawing Sheets

U.S. PATENT DOCUMENTS

| | | | | |
|---|---|---|---|---|
| 6,361,546 | B1* | 3/2002 | Khosravi | 606/200 |
| 6,368,338 | B1* | 4/2002 | Konya et al. | 606/200 |
| 6,499,487 | B1 | 12/2002 | McKenzie et al. | |
| 6,566,552 | B2 | 5/2003 | Tinti et al. | |
| 6,585,756 | B1* | 7/2003 | Strecker | 623/1.16 |
| 6,592,546 | B1 | 7/2003 | Barbut et al. | |
| 6,592,557 | B2 | 7/2003 | Barbut | |
| 6,595,980 | B1 | 7/2003 | Barbut | |
| 6,635,046 | B1* | 10/2003 | Barbut | 604/507 |
| 6,652,505 | B1* | 11/2003 | Tsugita | 604/509 |
| 6,652,555 | B1* | 11/2003 | VanTassel et al. | 606/200 |
| 6,702,773 | B1 | 3/2004 | Macoviak et al. | |
| 6,712,806 | B2 | 3/2004 | St. Germain et al. | |
| 6,743,196 | B2 | 6/2004 | Barbut et al. | |
| 7,128,073 | B1* | 10/2006 | van der Burg et al. | 128/887 |
| 2001/0044629 | A1* | 11/2001 | Stinson | 606/108 |
| 2003/0208224 | A1* | 11/2003 | Broome | 606/200 |
| 2004/0093015 | A1 | 5/2004 | Ogle | |
| 2005/0070952 | A1* | 3/2005 | Devellian | 606/200 |
| 2006/0184185 | A1* | 8/2006 | Olausson et al. | 606/152 |

OTHER PUBLICATIONS

Barbut et al., "Perfusion Augmentation Using Controlled Aortic Construction", 27th International Stroke—Conference, Feb. 7-9, 2002, Stroke—Jounral of the American Heart Association, vol. 33, No. 1, Jan. 2002, http://www.coaxia.com/article_02.htm, 2 pgs.

Carr, "Brain Science, CoAxia Aims to Tackle the $45 Billion Stoke Market", Twin Cities Business Monthly, Nov. 2002, http://www.coaxia.com/article_01.htm, 2 pgs.

Gomez et al., "Augmenting Cerebral Perfusion in Stroke Using Controlled Aortic Obstruction: A Feasibility Study", 28th International Stroke Conference, Stroke—Journal of the American Heart Association, vol. 34, No. 1, Jan. 2003, http://www.coaxia.com/article_05.htm, 2 pgs.

HeartCenterOnline for Patients, "Device Diverts Blood to Brain During Stroke", Reuters Health, Feb. 9, 2004, http://www.heartcenteronline.com/myheartdr/home/research-detail.cfm?reutersid+4124, 2 pgs.

Medtronic, "Carmeda® BioActive Surface*", Medtronic, Inc. 2004, Version B3.01, http://www.medtronic.com/cardsurgery/arrested_heart/carmeda_bioactive.html, 2 pgs.

Middleton et al., "Synthetic Biodegradable Polymer as Medical Devices", Medical Plastics and Biomaterials Magazine MPB Article Index, Mar. 1998 http://devicelink.com/mpb/archieve/98/03/002.html, 13 pgs.

Walters, "Intracranial Pressure and Cerebral Blood Flow", Physiology, Issue 8 (1998) Article 4, http://www.nda.ox.ac.uk/wfsa/html/u08_013.htm, 11 pgs.

Lylyk, "Aortic Obstruction. A New Treatment for Symptomatic Vasospasm Associated with Ruptured Aneurysm?", The Sixth Joint Meeting of the AANS/CNS Section on Cerebrovascular Surgery and the American Society of Interventional & Therapeutic Neuroradiology—Feb. 15-19, 2003; Phoenix, Arizona; 1 page.

Lylyk, "Treatment of Symptomatic Vasospasm with Partial Aortic Obstruction Using the Neuroflo Catheter," EREI, Presentation No. 378, Buenos Aires, Argentina, 1 page.

Kerr, "Device Diverts Blood to Brain During Stroke," Reuters, Feb. 6, 2004, 1 page.

* cited by examiner

DIVERSION DEVICE TO INCREASE CEREBRAL BLOOD FLOW

FIELD OF THE INVENTION

The present invention relates generally to devices and methods for providing temporary partial obstruction of aortic blood flow, with a resulting increase in cerebral blood flow. More particularly, the invention provides a device with a membrane for partially occluding an artery.

BACKGROUND

Stroke is a disruption of blood to a portion of the brain. The two main mechanisms are occlusion of a blood vessel (ischemic stroke) or hemorrhage of a blood vessel (hemorrhagic stroke). Ischemic stroke is significantly more common. Current state of the art treatment for ischemic stroke includes the injection of tissue plasminogen activator (tPA) within four hours of the event. Some evidence also points to a benefit from tPA out to 12 hours. Alternate therapies include mechanical dislocation or retrieval of the clot. These treatments are effective because the brain has significant collateral blood flow. Thus, when the primary blood supply to an area is disrupted, collateral flow provides some amount of oxygen to the affected tissue. The quantity is dependent on the size of the vessel obstructed, the location of the obstruction, blood oxygen level, and cerebral blood flow volume. The model for this situation is an area of dead tissue (infarction) that is dead and unrecoverable. Surrounding this tissue is the penumbra; a zone of oxygen depleted tissue. This tissue ranges from dying tissue through tissue experiencing insignificant oxygen level drops. Clearly within this continuum there exists tissue that is not dead but is not functioning due to oxygen deficit. Stroke intervention is thus intended to recover as much of the penumbra as possible, limiting the amount of tissue killed in the brain.

One solution to increasing the effectiveness of treatment is to increase the amount of oxygen delivered via collateral blood flow. Unlike some parts of the body, increasing blood pressure does not generally increase flow to the brain. A solution proposed in U.S. Pat. No. 6,743,196, to Barbut et al., is to insert a balloon into the aorta to partially occlude the aorta above the renal arteries as a means of increasing cerebral blood flow. Limitations of this device and method include mechanical complexity, constant monitoring requirements, and maintaining arterial access for the length of its use. Additionally, an inherent drawback with using a balloon to occlude a vessel is that balloons are always susceptible to failure (e.g., popping, leaking).

A device that is to be placed in an artery must address additional concerns compared to devices placed in veins because of the hemodynamic differences between arteries and veins. Arteries are much more flexible and elastic than veins and, in the arteries, blood flow is pulsatile with large pressure variations between systolic and diastolic flow. These pressure variations cause the artery walls to expand and contract. Blood flow rates in the arteries vary from about 1 L/min to about 5 L/min.

A need exists for a less complex, easily delivered, temporary arterial occlusion device that partially occludes an artery to increase cerebral blood flow, while avoiding the drawbacks of the prior devices. An associated filter that captures embolic material would be advantageous as well.

SUMMARY OF THE INVENTION

The present invention provides devices and methods for temporarily increasing cerebral blood flow. More specifically, a vascular occlusion, obstruction and/or constriction device is disclosed. The terms occlusion, obstruction, and constriction are used interchangeably herein to refer to partial or complete blockage of a vessel, and to any of the devices that provide such blockage. The devices include an occluding, obstructing, or constricting mechanism. In some embodiments, the devices include a filtration mechanism to trap emboli. The devices are collapsible and expandable to facilitate insertion into and removal from the vessel.

In one embodiment, the device includes an expandable frame with a membrane mounted on a first portion of the frame. The membrane has at least one opening. In some embodiments, the membrane has an outer region and an inner region, and an opening in the inner region. In use, the frame expands to conform to the inner walls of the aorta and the membrane at least partially occludes the aorta thereby increasing cerebral perfusion. The frame can include one or more anchors to aid in maintaining the device in position against the arterial blood flow pressure.

In another embodiment, the membrane is biodegradable such that upon insertion of the device, the membrane provides partial occlusion of the aorta to increase cerebral blood flow. As the membrane biodegrades, cerebral blood flow gradually returns to a normal state. The frame of the device can then be removed.

In a further embodiment, the expandable frame is a mesh tube with a membrane extending across at least part of a first end of the tube. In some embodiments, the second end of the tube is covered by a mesh or other filtering means.

In use, the expandable filter device is inserted into the aorta and expanded such that the membrane extends across the aorta to partially occlude the aorta and increase cerebral blood flow. In some embodiments, the membrane is at least partially permeable to blood. In other embodiments, the membrane has an opening to allow a limited amount of blood flow through the device. In one embodiment, the opening is sized to receive a catheter, and the downstream end of the device has one or more openings sized to receive a catheter. A catheter can traverse the filter device to provide access to arteries and organs upstream of the filter device.

DETAILED DESCRIPTION

Figure 1:
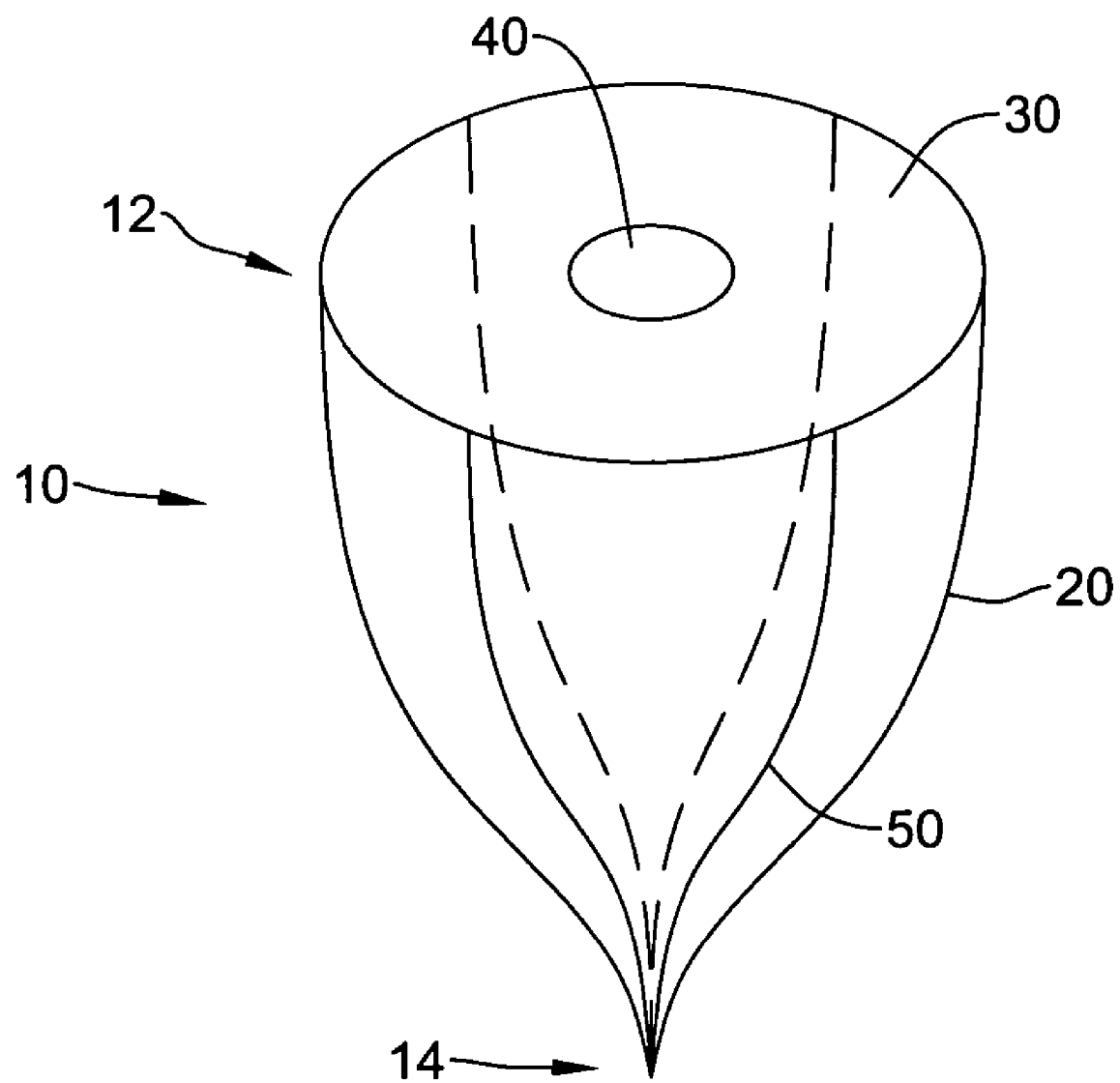
FIG. 1 shows an embodiment of a filter device according to the present invention.

The filter devices disclosed herein are characterized by their ability to withstand high arterial blood flow rates for an extended time and their ability to expand and contract with the wall of the aorta. In some embodiments, the devices are made of a material that is impermeable to blood such as TEFLON (polytetrafluoroethylene) or nitinol. The devices can have an anti-thrombogenic coating, such as heparin or Carmeda®. BioActive Surface (Carmeda Inc., U.S.). In other embodiments, the devices are made of a material that is permeable to blood, such as a mesh, woven material, or a thin polymer. All or a part of the device can be made of a biodegradable material. The device is collapsible and expandable and can be delivered surgically, endoscopically, or percutaneously with cannulas or intravascular catheters. In one embodiment, the device is introduced through the femoral artery. In another embodiment, the device is introduced through the brachial artery.

The device can be left in the aorta permanently or the device can be removed after temporary placement. In addition to or instead of a friction fit of an expandable frame, the device can include one or more anchoring mechanisms, such as sutures, surgical clips, hooks, loops, spikes, pins, or adhesives. The device can be of any shape, such as conical, frustoconical, ogival, cylindrical, hemispherical, or modifications of such shapes. The device can be self-expanding or is can be expanded mechanically such as by a balloon. Self-expanding devices can be made of a shape memory metal such as nitinol. In one embodiment, the device is flexible and expandable to fit a variety of vessel sizes. In another embodiment, the device is sized for a specific vessel. Multiple devices of varying sizes can be packaged together.

The method of the invention involves the temporary partial occlusion of arterial blood flow and resulting diversion of blood flow to the brain. The device of the invention is inserted into the aorta at or below the aortic arch and above the femoral arteries. In one embodiment, the device is placed in the aorta in the region of the renal arteries. In another embodiment, the device is placed in the aortic arch below the common carotid artery and braciocephalic trunk. In a further embodiment, the device is placed in the celiac trunk. In a still further embodiment, the device can be placed in the vena cava.

A membrane covering at least part of a first portion of the device serves to partially occlude the vessel. In some embodiments, the membrane is at least partially permeable to blood. The level of permeability and/or surface area that is permeable to blood can be adjusted to vary the amount of occlusion and thus vary the amount of blood flow diverted to the brain. In other embodiments, the membrane has one or more openings. In these embodiments, the membrane may or may not be partially permeable to blood. The number and size of the openings can be varied to determine the amount of blood flow diverted to the brain.

In a first embodiment, a filter device for temporary partial occlusion of an artery is provided as shown in FIG. 1. The device 10 includes a frame 20 having a first portion 12 and a second portion 14, and a membrane 30 disposed over the first portion 12. The membrane 30 is attached to the frame 20 by any suitable means including sonic or laser welding or adhesive bonding. In some embodiments, the membrane 30 is at least partially permeable to blood. The membrane 30 can be biodegradable. In some embodiments, the biodegradable material is selected to degrade over a desired time range from a very short time to a very long time after the device is inserted. In one embodiment, the membrane 30 biodegrades upon contact with an enzymatic agent, wherein the enzymatic agent is injected to degrade the membrane after the patient's cerebral blood flow returns to a substantially normal level. In another embodiment, the membrane biodegrades when irradiated, wherein the membrane is irradiated after the patient's cerebral blood flow returns to a substantially normal level. In one embodiment, the membrane 30 is made of polyglycolide. In another embodiment, the membrane 30 is a thin membrane with one or more laser-cut holes to allow blood flow. The thin membrane can be made of poly(dioxanone). In the embodiment shown in FIG. 1, the membrane 30 has a single opening 40 substantially centrally located. Alternatively, the opening 40 can be located off-center, or the membrane can have multiple openings. The number, size and position of openings 40 in the membrane 30 are selected to achieve a desired amount of blood flow diversion to the brain.

In some embodiments, the frame 20 includes multiple support members, such as struts 50. The struts 50 can be compressible, expandable, or flexible. The frame 20 is at least partially expandable to conform to the lumen of a vessel. In one embodiment, the frame 20 is made of a super elastic material such as nitinol. In other embodiments, the frame 20 is made of titanium, TEFLON (golytetrafluoroethylene), stainless steel, ceramic, polymers, or mixtures of such materials. In still further embodiments, the frame 20 is made of a mesh or woven material. In some embodiments, the second, or downstream, portion of the frame 20 forms a filter to capture emboli and/or fragments of the biodegradable membrane.

Figure 2:
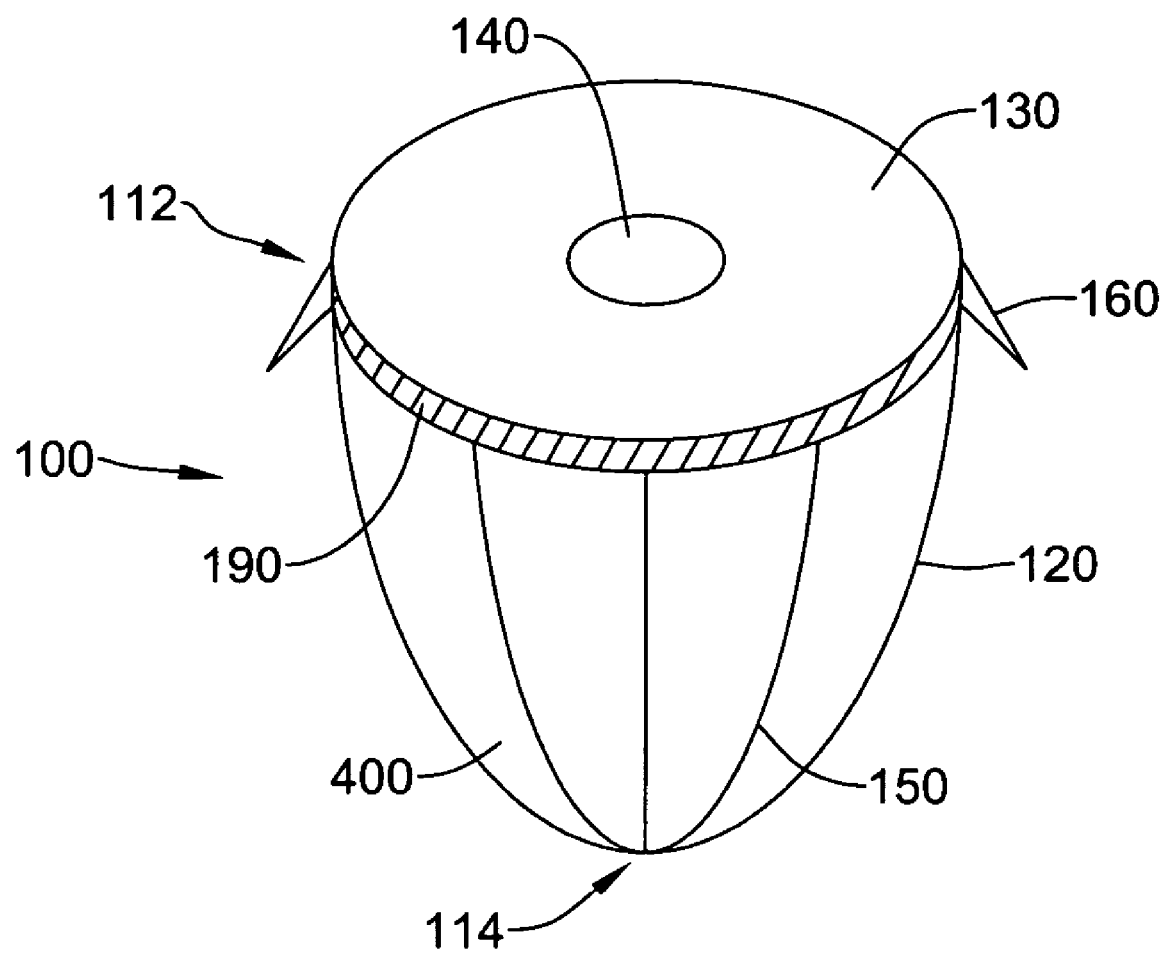
FIGS. 2-4 show additional embodiments of filter devices according to the present invention.
Figure 3:
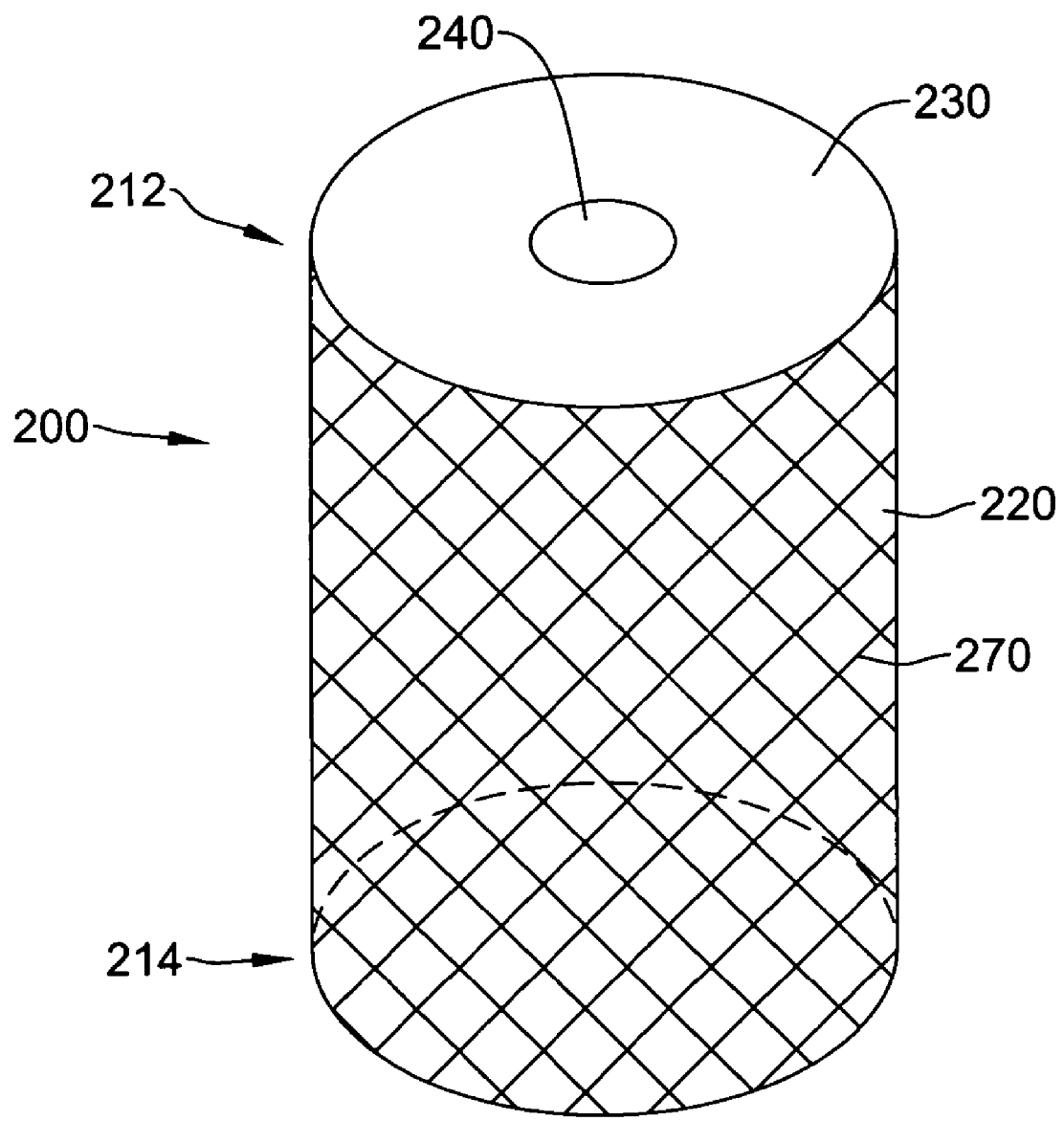

In another embodiment, shown in FIG. 3, the device 200 has a frame 220 and a membrane 230 with an opening 240 in the membrane 230. The frame 220 is a mesh tube 270 with a firstportion 212 and a second portion 214. In a still further embodiment, shown in FIG. 4, a device 300 has a frame 320, a membrane 330 and anchors 360. The frame 320 has a first portion 312 and a second portion 314 and the frame 320 is solid with an opening 380 in the second portion 314 of the frame 320. In embodiments with an open frame structure, such as those shown in FIGS. 1-3, the frame can be covered with a permeable material (for example, permeable material 400 on frame 20), such as a mesh, netting, or membrane to provide an additional filtration mechanism. In some embodiments, a permeable material covering the frame provides an additional mechanism to increase the occlusion of the artery and increase the blood flow to the brain.

Figure 4:
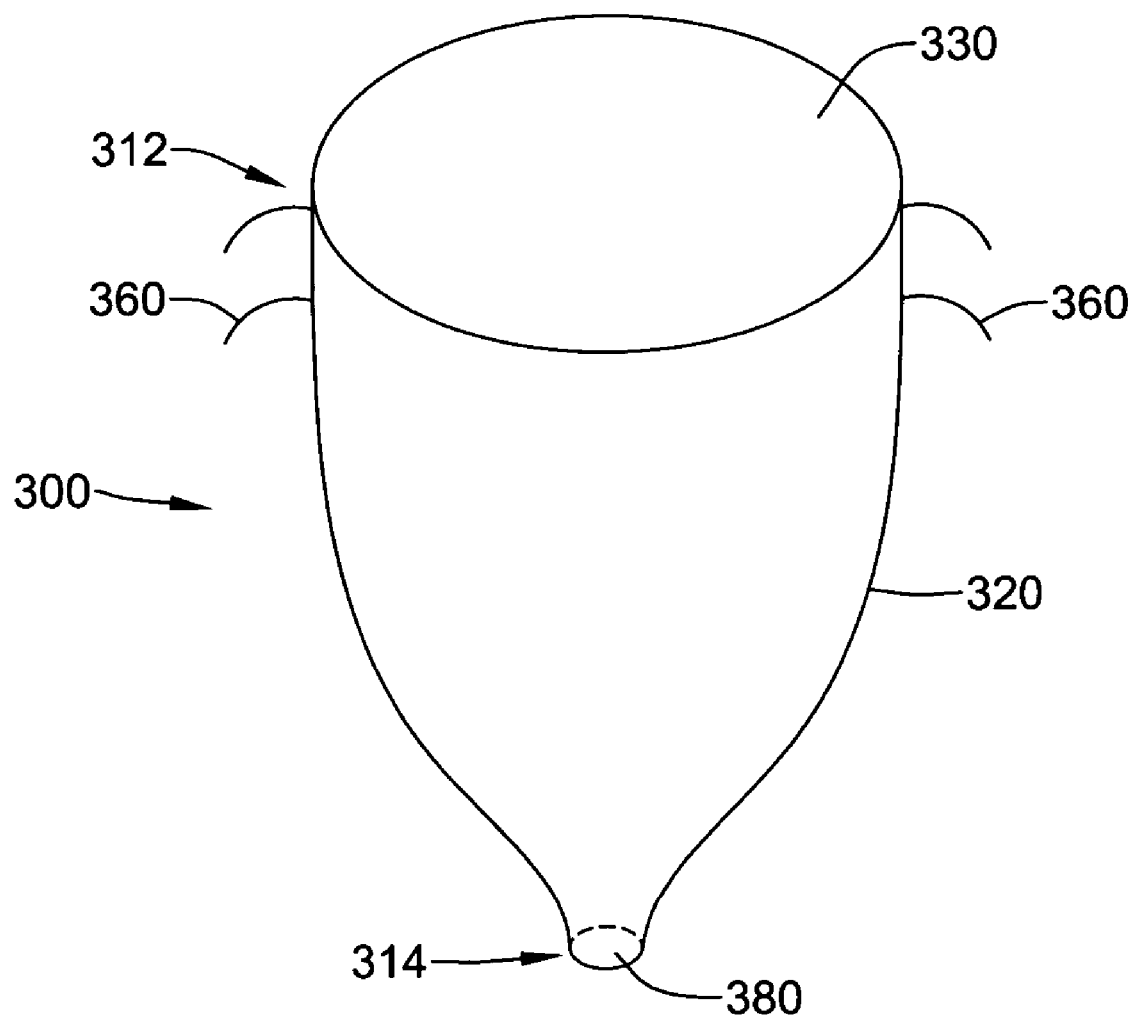

In devices having a tapered, angled, or cone shape, such as those shown in FIGS. 1, 2, and 4, at least the first end 12, 112, 312, is expandable. In one embodiment, shown in FIG. 2, the device 100 includes a frame 120 with struts 150, the frame 120 having a first portion 112 and a second portion 114. The frame 120 includes a flexible or expandable band or ring 190 on the first portion 112. The flexible ring 190 can aid in attaching the membrane 130 to the frame 120, and the membrane 130 has an opening 140. In another embodiment, the flexible ring 190 is attached to the frame 120 and the membrane 130 is attached to the ring 190.

One or more anchors 160 can be included to aid in securing the device in the vessel. The anchors 160 can be hooks, spikes, loops, pins or any other protrusion sufficient to secure the device in the vessel. In one embodiment, the anchors 160 are mechanically retractable. In another embodiment, the anchors 160 are made of a deformable, flexible, or super elastic material, and are removable from a vessel wall by compressing or folding the frame 20. The anchors 160 can be attached to the frame 20, struts 50, ring 190, or permeable material 400.

Figure 5:
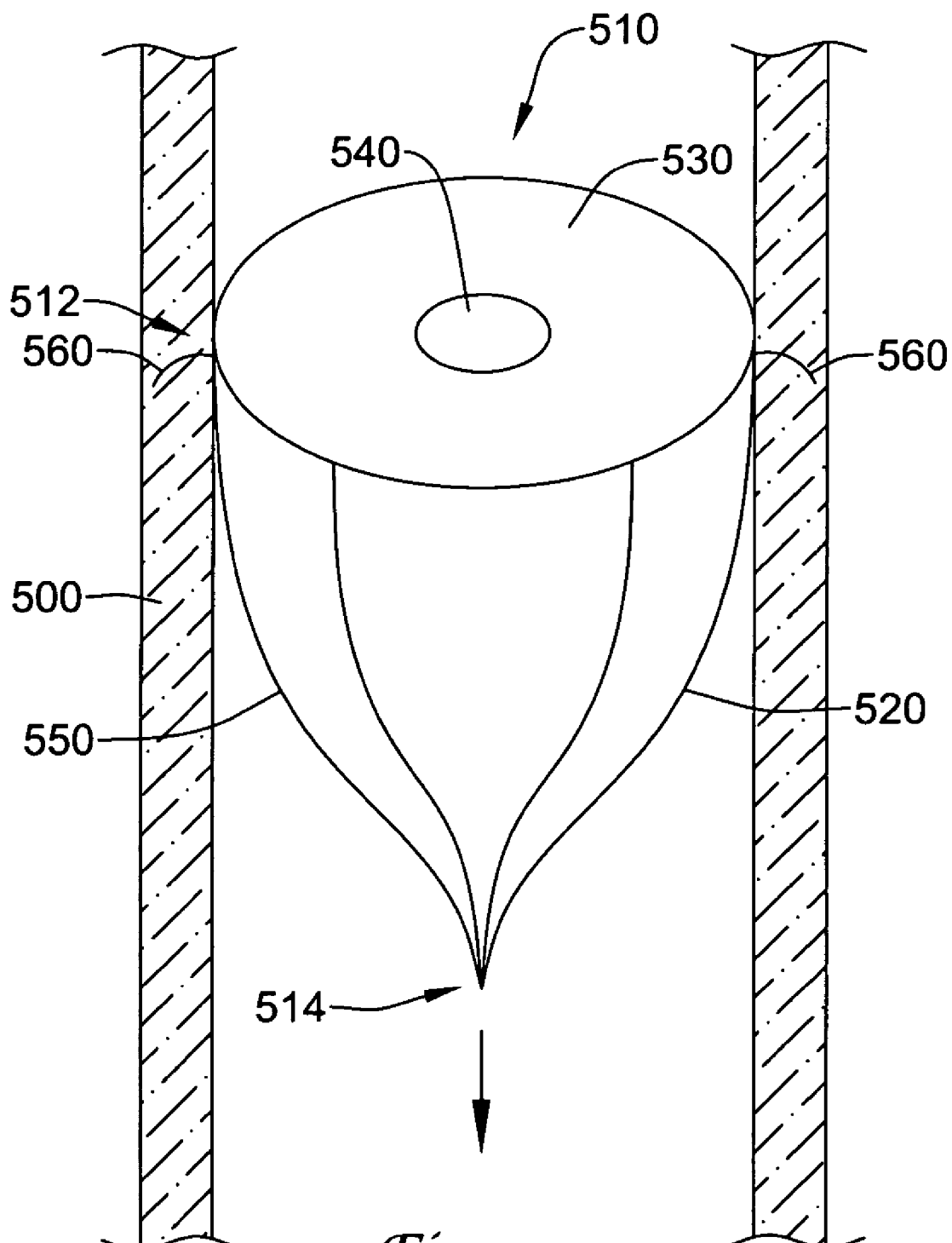
FIG. 5 shows a filter device according to the present invention in place in a vessel.

FIG. 5 shows a partial occlusion device 510 in place in the aorta. The device 510 includes a frame 520 made up of struts 550. The frame 520 has a first portion 512 and a second portion 514, and the first portion 512 of the frame 520 is covered by a membrane 530 with a central opening 540. Anchors 560 extend from the first portion 512 of the frame 520 into the vessel walls 500 to secure the device 510 against blood flow, which is indicated by the arrow.

A mixture of carbon dioxide and oxygen ($CO_2/O_2$) can be administered to the patient before, during, or after insertion of the filter device to provide additional blood flow to the brain. Enriching the blood content of $CO_2$ while maintaining a high oxygen level causes blood to be shunted to the brain.

Although the foregoing invention has, for the purposes of clarity and understanding, been described in some detail by way of illustration and example, it will be obvious that certain changes and modifications may be practiced with will still fall within the scope of the appended claims. Moreover, it will be understood that each and every feature described for any given embodiment or in any reference incorporated herein, can be combined with any of the other embodiments described herein.

We claim:

1. A partial aortic occlusion device, comprising:
an expandable frame having an upstream portion and a downstream portion, the frame defining a circular mouth in the upstream portion configured to expand when positioned substantially perpendicular to the direction of blood flow in an aorta having an aortic lumen defined by an aortic wall, such that the upstream portion substantially conforms to the aortic wall to thereby at least partially occlude the aorta and increase cerebral profusion, wherein the downstream portion is substantially smaller in cross section than the expanded upstream portion, and the frame comprises a tapered transition between the upstream and downstream portions, such that the downstream portion is positioned in a central area of the aortic lumen without contacting the aortic wall when the circular mouth of the upstream portion is positioned in the aorta generally transverse to a line joining the upstream and downstream portions;
a membrane mounted across at least a part of the circular mouth, the membrane having a continuous outer annular region adjacent the frame, said continuous outer region defining an opening, wherein the membrane is impermeable to blood and is biodegradable; and
a permeable filtering material disposed on the downstream portion of the expandable frame, the filtering material configured to capture emboli and fragments of the biodegradable membrane entering the downstream portion through the circular mouth in the upstream portion.

2. The partial aortic occlusion device of claim 1, wherein the frame includes one or more anchors configured to removably attach the device to a wall of the aorta.

3. The partial aortic occlusion device of claim 1, wherein the expandable frame is made of super elastic material.

4. The partial aortic occlusion device of claim 1, wherein the expandable frame includes at least two struts, the struts spaced apart in the upstream portion of the frame and connected in the downstream portion of the frame.

5. The partial aortic occlusion device of claim 4, wherein at least two struts include one or more anchors configured to removably attach the device to a wall of the aorta.

6. The partial aortic occlusion device of claim 1, wherein the frame defines a distal end opening in the downstream portion, and wherein the distal end opening in the downstream portion and the opening defined by the membrane are sized to receive a catheter therethrough.

7. The partial aortic occlusion device of claim 1, wherein the membrane has two or more openings.

8. A method for temporarily increasing cerebral blood flow in a patient, comprising the steps of:
inserting an expandable filter device into the aorta, said filter device comprising an upstream portion having a circular mouth and a biodegradable membrane extending across the circular mouth, said filter device further comprising a downstream portion with a permeable filtering material disposed on the downstream portion,
wherein the circular mouth of the upstream portion is generally transverse to a line joining the upstream and downstream portions and the membrane extending across the circular mouth is impermeable to blood and further defines a central opening, and
expanding the filter device to partially occlude the aorta and increase cerebral blood flow wherein the biodegradable membrane degrades to allow aortic blood flow to gradually increase, and wherein the permeable filtering material disposed on the downstream portion is configured to capture fragments of the biodegradable membrane.

9. The method of claim 8, wherein the membrane biodegrades upon contact with an enzymatic agent, the method further comprising a step of injecting an enzymatic agent to degrade the membrane after the patient's cerebral blood flow returns to a substantially normal level.

10. The method of claim 8, wherein the membrane biodegrades when irradiated; the method further comprising a step of irradiating the membrane after the patient's cerebral blood flow returns to a substantially normal level.

11. The method of claim 8, wherein the filter device is inserted in the aorta above the renal arteries.

12. The method of claim 8, wherein the filter device is inserted below the common carotid artery and brachiocephalic trunk.

13. The method of claim 8, further comprising a step of removing the filter device after the membrane biodegrades.

14. The method of claim 8, wherein the opening in the membrane is sized to receive a catheter and the downstream portion of the device has one or more openings sized to receive a catheter; such that a catheter can traverse the filter device to provide access to arteries and organs upstream of the filter device.

15. The method of claim 8, wherein the filter device is coated with a non-thrombogenic agent.

16. The method of claim 8, further comprising a step of administering a $CO_2/O_2$ mixture to the patient.

17. A method for temporarily increasing cerebral blood flow in a patient, comprising the steps of:
inserting an expandable filter device into the aorta, the filter device including a first portion having a circular mouth and an occlusive membrane that biodegrades in the presence of radiation extending across the circular mouth, and the filter device including a second portion with a permeable filtering material disposed on the second portion;
expanding the filter device to partially occlude the celiac trunk and increase cerebral blood flow;
wherein the second portion is configured to capture emboli and fragments of the biodegradable membrane, and
irradiating the membrane after the patient's cerebral blood flow returns to a substantially normal level to allow aortic blood flow to gradually increase.

18. A partial aortic occlusion device, comprising:
an expandable frame having an upstream portion and a downstream portion, the frame defining a circular mouth in the upstream portion configured to expand when positioned substantially perpendicular to the direction of blood flow in an aorta having an aortic lumen defined by an aortic wall, such that the upstream portion substantially conforms to the aortic wall to thereby at least partially occlude the aorta and increase cerebral profusion;
wherein the circular mouth of the upstream portion is generally transverse to the downstream portion;
an occlusive membrane mounted across at least a part of the circular mouth, the membrane having an outer annular region defining an opening in the occlusive membrane, wherein the membrane is biodegradable in the presence of an enzymatic agent; and a permeable filtering material disposed on the downstream portion of the expandable frame; the filtering material configured to capture emboli and fragments of the biodegradable membrane entering the downstream portion through the circular mouth of the upstream portion wherein the downstream portion of the expandable frame has at least one longitudinal region of smaller diameter than the upstream portion of the expandable frame wherein the expandable frame tapers to form a generally conical shape, and wherein blood, exclusive of emboli and other debris, which enters the circular mouth, passes through the permeable filtering material.

19. The partial aortic occlusion device of claim 18, wherein the occlusive membrane includes a region that is partially permeable.

20. The partial aortic occlusion device of claim 18, wherein the frame includes one or more anchors configured to removably attach the device to the aortic wall.

21. The partial aortic occlusion device of claim 18, wherein the expandable frame is made of super elastic material.

22. The partial aortic occlusion device of claim 18, wherein the expandable frame includes at least two struts, the struts spaced apart in the upstream portion of the frame and connected in the downstream portion of the frame.

23. The partial aortic occlusion device of claim 18, wherein the frame has at least one opening in the downstream portion, and the opening in the downstream portion and the opening in the membrane are sized to receive a catheter therethrough.

* * * * *